United States Patent
Skujins et al.

(10) Patent No.: US 11,160,570 B2
(45) Date of Patent: Nov. 2, 2021

(54) ASPIRATION FLOW SENSOR

(71) Applicant: Covidien LP, Mansfield, MA (US)

(72) Inventors: Peter Skujins, Laguna Hills, CA (US);
Eric Mintz, Costa Mesa, CA (US);
Ujwal Jalgaonkar, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 81 days.

(21) Appl. No.: 16/381,809

(22) Filed: Apr. 11, 2019

(65) Prior Publication Data

US 2020/0323546 A1 Oct. 15, 2020

(51) Int. Cl.
*A61B 17/22* (2006.01)
*A61M 1/00* (2006.01)
*A61B 17/00* (2006.01)

(52) U.S. Cl.
CPC .............. *A61B 17/22* (2013.01); *A61M 1/76* (2021.05); *A61M 1/84* (2021.05); *A61M 1/86* (2021.05);
(Continued)

(58) Field of Classification Search
CPC .............. A61B 17/22; A61B 17/22004; A61B 2017/22079; A61B 34/76; A61B 18/24; A61B 2017/00022; A61B 2017/22007–22009; A61B 2017/22011; A61B 2017/22024; A61B 2017/22025; A61B 10/0283; A61B 5/150053; A61B 5/150145; A61B 5/150099; A61B 5/150083; A61B 5/150061; A61M 1/0086; A61M 1/0039; A61M 1/008; A61M 1/1006; A61M 1/101; A61M 1/0023–0056; A61M 1/0025; A61M 1/0031; A61M 1/0058–0064; A61M 1/0066–0076; A61M 2205/3334; A61M 2205/582; A61M 1/00; A61M 2205/3344; A61M 1/71–985; A61M 1/77; A61M 1/772; A61M 1/92; A61M 1/73; A61M 2205/332; A61M 2206/20; A61M 3/0275;
(Continued)

(56) References Cited

U.S. PATENT DOCUMENTS 3,698,245 A 10/1972 McNabb
3,855,859 A 12/1974 Adams
(Continued)

FOREIGN PATENT DOCUMENTS

WO 2014151209 A1 9/2014
WO 2018096182 A2 5/2018

OTHER PUBLICATIONS

Miloro et al., "Removing vascular obstructions: a challenge, yet an opportunity for interventional microdevices," Biomedical Microdevices, Feb. 2012, 25 pages.
(Continued)

*Primary Examiner* — Kathleen S Holwerda
*Assistant Examiner* — Lauren Dubose
(74) *Attorney, Agent, or Firm* — Shumaker & Sieffert, P.A.

(57) ABSTRACT

In some examples, an aspiration system a catheter and a fluid flow sensor. The fluid flow sensor includes a fluid inlet, a fluid outlet, and a flow oscillator. The fluid inlet is configured to receive fluid from the catheter. The flow oscillator configured to oscillate flow of the fluid through the fluid flow sensor to generate flow-induced vibrations. The fluid outlet is configured to discharge the fluid.

17 Claims, 4 Drawing Sheets

(52) U.S. Cl.
CPC ............... *A61B 2017/00022* (2013.01); *A61B 2017/0084* (2013.01); *A61B 2017/00778* (2013.01); *A61B 2017/00893* (2013.01); *A61B 2017/22079* (2013.01); *A61M 2205/0222* (2013.01); *A61M 2205/0238* (2013.01); *A61M 2205/3334* (2013.01); *A61M 2205/3344* (2013.01); *A61M 2205/582* (2013.01); *A61M 2206/20* (2013.01)

(58) Field of Classification Search
CPC ......... A61M 2005/16863; A61M 2005/16868; A61M 2005/16872; G01F 1/3227
USPC ........................................ 606/127, 159, 200
See application file for complete search history.

(56) References Cited

U.S. PATENT DOCUMENTS

| | | | |
|---|---|---|---|
| 4,085,615 A | | 4/1978 | Haefner et al. |
| 4,244,230 A | * | 1/1981 | Bauer .................... G01F 1/3227 73/861.19 |
| 4,409,851 A | * | 10/1983 | Bahrton .................... G01P 5/01 73/861.21 |
| 4,921,477 A | | 5/1990 | Davis |
| 4,984,461 A | * | 1/1991 | Haynes .................... G01F 3/16 73/249 |
| 5,186,431 A | | 2/1993 | Tamari |
| 5,298,886 A | * | 3/1994 | Ueki .................... G01F 1/3227 340/606 |
| 6,179,808 B1 | | 1/2001 | Boukhny et al. |
| 6,740,058 B2 | | 5/2004 | Lal et al. |
| 9,038,481 B2 | | 5/2015 | Schiferli |
| 10,108,266 B2 | | 10/2018 | Banerjee et al. |
| 10,563,776 B1 | * | 2/2020 | Lindsay .................. F16K 51/00 |
| 2004/0244498 A1 | | 12/2004 | Chen et al. |
| 2011/0094308 A1 | | 4/2011 | Vaidya |
| 2013/0110085 A1 | * | 5/2013 | Adamson .......... A61M 25/0043 604/523 |
| 2013/0165944 A1 | | 6/2013 | Gal et al. |
| 2013/0245980 A1 | | 9/2013 | Forbes et al. |
| 2013/0274712 A1 | | 10/2013 | Schecter |
| 2015/0283309 A1 | | 10/2015 | Look et al. |
| 2016/0220741 A1 | * | 8/2016 | Garrison ................ A61M 1/008 |
| 2017/0056032 A1 | | 3/2017 | Look et al. |
| 2017/0181760 A1 | * | 6/2017 | Look ................... A61M 1/0031 |
| 2017/0196478 A1 | | 7/2017 | Hunter |

OTHER PUBLICATIONS

McDonough et al., "Effect of geometrical parameters on flow-switchingfrequencies in 3D printed fluidic oscillatorscontaining different liquids," Elsevier, accepted Oct. 27, 2016, 12 pp.

Mosley et al., "Design and Dynamics of a Shape Memory Alloy Wire Bundle Actuator," Proceedings of the ANS, 8th Topical Meeting on Robotics and Remote Systems, 1999, 14 pp. (Applicant points out, in accordance with MPEP 609.04(a), that the year of publication, 1999, is sufficiently earlier than the effective U.S. filing date, so that the particular month of publication is not in issue.).

Dynalloy, Inc., "Technical Characteristics of Flexinol," accessed from http://www.dynalloy.com/pdfs/TCF1140.pdf accessed on or about Jan. 2019, 12 pp.

International Search Report and Written Opinion of International Application No. PCT/US2020/024465, dated Jun. 9, 14 pp.

* cited by examiner

ASPIRATION FLOW SENSOR

TECHNICAL FIELD

This disclosure relates to medical aspiration.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels. This treatment may involve drawing fluid through the medical catheter.

SUMMARY

In some aspects, this disclosure describes example fluid flow sensors and systems that include a catheter and a fluid flow sensor. The fluid flow sensor includes a fluid inlet configured to receive fluid from the catheter and a fluid outlet configured to discharge the fluid. The fluid flow sensor also includes a flow oscillator configured to oscillate flow of the fluid through the fluid flow sensor to generate flow-induced vibrations. This disclosure also describes examples of methods of using the fluid flow sensors and systems including the fluid flow sensors.

Clause 1: In one example, an aspiration system comprises: a catheter; and a fluid flow sensor comprising: a fluid inlet configured to receive fluid from the catheter; a fluid outlet configured to discharge the fluid; and a flow oscillator configured to oscillate flow of the fluid through the fluid flow sensor to generate flow-induced vibrations.

Clause 2: In some examples of the aspiration of clause 1, the flow oscillator further comprises: a flow diverting portion configured to oscillate the flow of the fluid between the fluid inlet and the fluid outlet to generate an oscillating pressure differential; and an oscillating portion downstream of the flow diverting portion and configured to oscillate in response to the oscillating pressure differential.

Clause 3: In some examples of the aspiration system of clause 2, the oscillating portion comprises at least one of a flap, a roller, a ball, or a paddle.

Clause 4: In some examples of the aspiration system of any of clauses 1-3, the flow oscillator is configured to generate vibrations capable of haptic detection by a human for flow in a first direction and generate vibrations that are not capable of haptic detection by a human for flow in a second direction.

Clause 5: In some examples of the aspiration system of any of clauses 1-4, the flow oscillator is configured to oscillate the flow of the fluid above an oscillation threshold in a first flow direction and not oscillate the flow of the fluid above the oscillation threshold in a second flow direction.

Clause 6: In some examples of the aspiration system of any of clauses 1-5, each of the fluid inlet and the fluid outlet are configured to couple to aspiration tubing.

Clause 7: In some examples of the aspiration system of clause 6, the flow oscillator further comprises at least one channel, and wherein a cross-sectional area of the at least one channel is greater than a cross-sectional area of an inner lumen of the aspiration tubing.

Clause 8: In some examples of the aspiration system of any of clauses 1-7, the flow oscillator further comprises defines at least one channel, and wherein an inner diameter of the at least one channel is greater than an inner diameter of the catheter.

Clause 9: In some examples of the aspiration system of any of clauses 1-8, the flow oscillator further comprises: at least one primary channel configured to pass a majority of the flow of the fluid; and at least two secondary channels each configured to divert a portion of the flow of the fluid from a downstream portion of the at least one primary channel to an upstream portion of the at least one primary channel.

Clause 10: In some examples of the aspiration system of any of clauses 1-9, the aspiration system further comprises a pressure sensor mechanically coupled to the fluid flow sensor and configured to detect vibrations from the fluid flow sensor indicating flow of the fluid through the fluid flow sensor.

Clause 11: In some examples of the aspiration system of clause 10, the pressure sensor is configured to communicatively couple to a notification system configured to generate a notification in response to detecting the flow of the fluid.

Clause 12: In some examples of the aspiration system of any of clauses 1-11, the flow oscillator is configured to generate vibrations having a frequency of about 15 hertz to about 30 hertz at a flow rate of the fluid of about 3 milliliters per second to about 5 milliliters per second.

Clause 13: In some examples of the aspiration system of any of clauses 1-12, the flow oscillator is configured to increase a magnitude of the vibrations in response to an increase in a flow rate of the fluid through the flow oscillator.

Clause 14: In some examples of the aspiration system of any of clauses 1-13, the flow oscillator is configured to increase a frequency of the vibrations in response to an increase in a flow rate of the fluid through the flow oscillator.

Clause 15: In some examples of the aspiration system of any of clauses 1-14, the aspiration system further comprises a fluid switch configured to start and stop the flow of the fluid through the flow oscillator.

Clause 16: In some examples of the aspiration system of clause 15, the fluid switch is upstream of the fluid flow sensor.

Clause 17: In some examples of the aspiration system of clause 16, the fluid switch is coupled to the flow oscillator by less than ten centimeters aspiration tubing.

Clause 18: In some examples of the aspiration system of any of clauses 1-17, the catheter is upstream of the fluid flow sensor, the system further comprising a fluid pump downstream of the fluid flow sensor and configured to generate a suction through the catheter.

Clause 19: In some examples of the aspiration system of any of clauses 1-18, the flow oscillator is coated with at least one of an anti-thrombogenic material or a lubricious material.

Clause 20: In one example, a fluid flow sensor comprises: a fluid inlet configured to receive fluid from a catheter; an inlet connector proximate to the fluid inlet and configured to couple to at least one of aspiration tubing or a fluid switch; a fluid outlet configured to discharge the fluid; an outlet connector proximate to the fluid outlet and configured to couple to aspiration tubing; and a flow oscillator configured to oscillate flow of the fluid through the fluid flow sensor to generate flow-induced vibrations.

Clause 21: In some examples of the fluid flow sensor of clause 20, the flow oscillator further comprises: a flow diverting portion configured to oscillate the flow of the fluid between the fluid inlet and the fluid outlet to generate an oscillating pressure differential; and an oscillating portion downstream of the flow diverting portion and configured to oscillate in response to the oscillating pressure differential.

Clause 22: In some examples of the fluid flow sensor of clause 20 or 21, the flow oscillator is configured to oscillate the flow of the fluid above an oscillation threshold in a first flow direction and not oscillate the flow of the fluid above the oscillation threshold in a second flow direction.

Clause 23: In one example, a method comprises: introducing a catheter into vasculature of a patient, the catheter coupled to a fluid flow sensor comprising: a fluid inlet configured to receive fluid from a catheter; a fluid outlet configured to discharge the fluid; and a flow oscillator configured to oscillate flow of the fluid through the fluid flow sensor to generate flow-induced vibrations; and after introducing the catheter into the vasculature of the patient, aspirating a fluid through the catheter.

Clause 24: In some examples of the method of clause 23, the method further comprises during the aspirating, generating, by the flow oscillator, the flow-induced vibrations in response to flow of the fluid through the flow oscillator from catheter.

Clause 25: In some examples of the method of clause 24, the method further comprises during the aspirating and in response to an increase in at least one of a magnitude or frequency of the flow-induced vibrations, repositioning the catheter in the vasculature of the patient.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
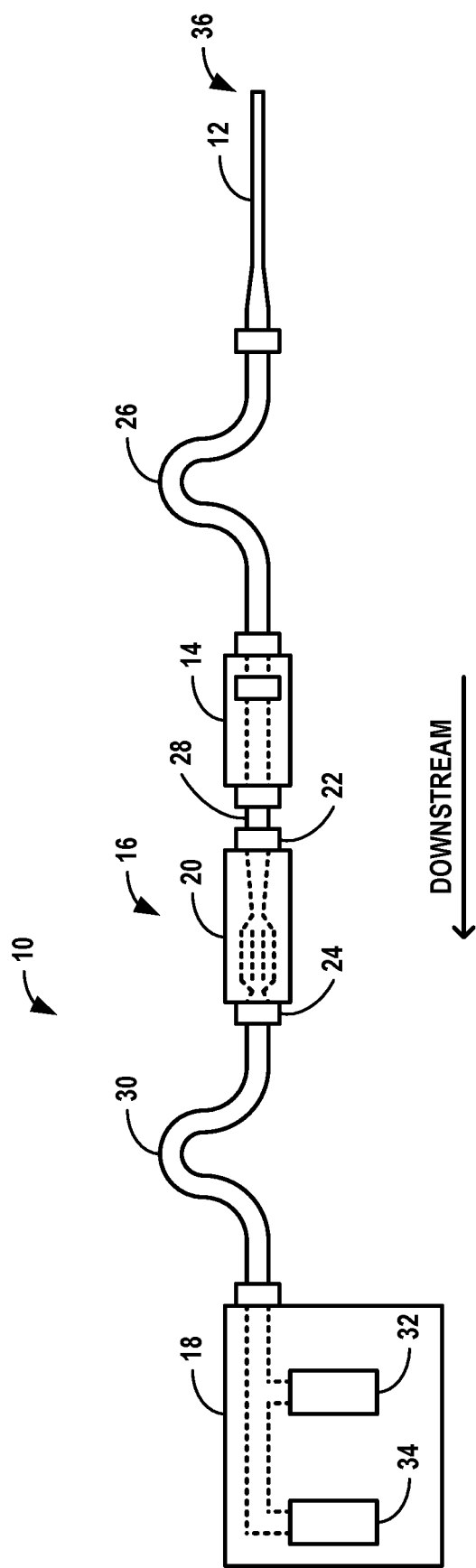
FIG. 1 is a schematic diagram illustrating an example aspiration system that includes a fluid flow sensor configured to generate flow-induced vibrations in response to receiving fluid flow from a catheter.

The disclosure describes certain embodiments including a fluid flow sensor configured to generate haptic feedback that indicates and is driven by fluid flow from a catheter or through an aspiration system, as well as aspiration systems including the fluid flow sensor and the catheter and methods of using the aspiration systems.

Thrombosis occurs when a thrombus (e.g., a blood clot or other embolus) forms and obstructs vasculature of a patient. To treat a patient with thrombosis, a clinician may position an aspiration catheter in a blood vessel of the patient near the thrombus, apply suction to the aspiration catheter, and engage the thrombus with a tip of the aspiration catheter. Once the tip of the aspiration catheter has engaged the thrombus, the clinician may remove the aspiration catheter with the thrombus attached to the tip or suction off pieces of the thrombus until the thrombus is removed from the blood vessel of the patient. The aspiration of the thrombus may be part of an aspiration procedure, such as, but not limited to, a medical procedure using A Direct Aspiration first Pass Technique (ADAPT) for acute stroke thrombectomy, or any other aspiration of thrombus or other material from the neurovasculature or other blood vessels.

During placement of the aspiration catheter, a clinician may first position the aspiration catheter proximate an estimated location of the thrombus using a visual aid, such as an x-ray display or other medical imaging technique, and begin suctioning fluid through a lumen of the aspiration catheter into a canister. The clinician may reposition the aspiration catheter until the tip of the aspiration catheter encounters the thrombus. If the thrombus is relatively hard and fibrous, then the thrombus may block the distal opening of the catheter lumen (e.g., at a tip of the aspiration catheter) and cause a reduction or cessation of flow through the lumen of the aspiration catheter. If the thrombus is relatively soft, then the thrombus may initially block the distal opening of the catheter lumen until the thrombus begins to break apart in response to the application of the vacuum force, which may cause an initial reduction or cessation of flow through the catheter lumen followed by a continuous or increased flow through the catheter lumen as the thrombus is sucked piecemeal from the vasculature. In either case, engagement of the thrombus may cause a change in flow characteristics, such as flow rate, of fluid through the catheter lumen.

The clinician performing the medical aspiration may use the change in flow characteristics of the suctioned fluid through an inner lumen of the aspiration catheter as an indication that the aspiration catheter is engaged with the thrombus and/or has removed the thrombus. For example, the clinician may visually confirm that suction has reduced as the thrombus is engaged by observing a decrease in a flow of fluid into the canister, visually confirm that suction has increased as the thrombus is removed by observing an increase in a flow of fluid into the canister, reposition the aspiration catheter, e.g., using the medical image, and continue to visually confirm the flow characteristics and reposition the aspiration catheter as needed until the flow of fluid is constant or the thrombus is removed. Due to this alternating visual confirmation of flow characteristics, the clinician may divert her gaze and attention from the medical image display, the patient, or other devices to an apparatus containing the aspirated fluid, such as a canister or tubing. Additionally, visual confirmation of an opaque or semi-opaque liquid by the clinician, such as blood, may be relatively difficult in some circumstances, such as a medical procedure room that is relatively dimly lit to enable better viewing of the medical image by the clinician.

In examples described in this disclosure, an aspiration system may include a fluid flow sensor configured to provide a tactile indication of fluid flow through an inner lumen of an aspiration catheter that is directly produced by the fluid flow. The fluid flow sensor may include a flow oscillator configured to oscillate flow of the fluid through the fluid flow sensor to generate flow-induced vibrations. These flow-induced vibrations provide haptic feedback to a clinician, e.g., may be sensed by a clinician holding the fluid flow sensor as an indication of a presence, absence, or change in fluid flow through the aspiration catheter. In this way, the clinician may detect fluid flow through the aspiration catheter without diverting her gaze to the aspiration tubing or fluid canister. The fluid flow sensor may be relatively small, reliable and/or relatively inexpensive, as the fluid flow sensor may have a reduced number or an absence of electronics or moving parts.

FIG. 1 is a schematic diagram illustrating an example aspiration system 10 that includes a fluid flow sensor 16 configured to generate flow-induced vibrations in response to fluid flow from a catheter 12. Aspiration system 10 includes catheter 12, a fluid flow switch 14 coupled to catheter 12 through aspiration tubing 26, fluid flow sensor 16 coupled to fluid switch 14 through aspiration tubing 28, and a fluid pump 18 coupled to fluid flow sensor 16 through aspiration tubing 30. Unless otherwise indicated, FIG. 1 will be described with respect to fluid flow in a first flow direction from catheter 12 to fluid pump 18, as indicated by the "downstream" arrow; however, as will be described below, fluid flow may proceed in a second flow direction, opposite the first flow direction.

Aspiration system 10 may be configured to draw fluid from catheter 12 into fluid pump 18. For example, a fluid, such as blood, an aspiration fluid, or a mixture thereof, may be drawn into at least one distal opening 36 of catheter 12 by negative pressure created by pump 18, distal opening 36 being an opening to the inner lumen of catheter 12. For example, the fluid may flow from catheter 12 through aspiration tubing 26, fluid flow switch 14, aspiration tubing 28, fluid flow sensor 16, and aspiration tubing 30 into fluid pump 18.

Aspiration system 10 includes catheter 12 upstream of fluid flow sensor 16. Catheter 12 includes an elongated body and a hub. The elongated body of catheter 12 is configured to be advanced through vasculature of a patient via a pushing force applied to a proximal portion of the elongated body with minimal or no buckling, kinking, or otherwise undesirably deforming (e.g., ovalization). Catheter 12 may include an inner liner, an outer jacket, and a structural support member, such as a coil and/or a braid, positioned between at least a portion of the inner liner and at least a portion of the outer jacket. Catheter 12 may include other structures, such as an expandable member configured to radially expand within a vessel of a patient, e.g., to engage a clot within the vessel. Catheter 12 may define at least one inner lumen.

Catheter 12 may be used as an aspiration catheter to remove a thrombus, such as a clot or other material such as plaques or foreign bodies, from vasculature of a patient. In such examples, a negative pressure may be applied, such as by fluid pump 18, to the proximal end of catheter 12 to draw a thrombus into the inner lumen of catheter 12 through one or more distal openings 36. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 12 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. The elongated body of catheter 12 may be structurally configured to be relatively flexible, pushable, and relatively kink- and buckle-resistant, so that it may resist buckling when a pushing force is applied to a relatively proximal section of catheter 12 to advance the elongated body distally through vasculature, and so that it may resist kinking when traversing around a tight turn in the vasculature. In some examples, the elongated body is configured to substantially conform to the curvature of the vasculature. In addition, in some examples, the elongated body has a column strength and flexibility that allows at least the distal portion of the elongated body to be navigated from a femoral artery, through the aorta of the patient, and into the intracranial vascular system of the patient, e.g., to reach a relatively distal treatment site. Alternatively, the elongated body can have a column strength (and/or be otherwise configured) to enable the distal portion of the elongated body to be navigated from a radial artery, through the aorta of the patient or otherwise to a common carotid or vertebral artery, and into the intracranial vascular system of the patient, e.g., to reach a relatively distal treatment site.

Although primarily described as being used to reach relatively distal vasculature sites, catheter 12 may also be configured to be used with other target tissue sites. For example, catheter 12 may be used to access tissue sites throughout the coronary and peripheral vasculature, the gastrointestinal tract, the urethra, ureters, fallopian tubes, veins and other body lumens.

In some examples, catheter 12 may be described in terms of the working length of the elongated body. The working length of catheter 12 may depend on the location of the target tissue site within the body of a patient or may depend on the medical procedure for which catheter 12 is used. For example, if catheter 12 is a distal access catheter used to access vasculature in a brain of a patient from a femoral artery access point at the groin of the patient, the elongated body may have a working length of about 115 centimeters (cm) to about 145 cm or more, such as about 130 cm, although other lengths may be used. The distal portion may be about 5 cm to about 35 cm in length. The proximal portion may be about 90 cm to about 130 cm in length, depending on the length of the distal portion.

In some cases, a clinician may steer catheter 12 through the vasculature of a patient by pushing or rotating the hub and/or the proximal portion of catheter 12 to navigate the distal portion of catheter 12 through the vasculature of a patient. The clinician may apply torque to the hub and/or the proximal portion of catheter 12 to rotate the distal portion of catheter 12. In some examples, as will be discussed further below, a clinician may guide catheter 12 using a first hand while controlling fluid flow from catheter 12 with fluid flow switch 14 and sensing fluid from catheter 12 with fluid flow sensor 16 using a second hand.

Aspiration system 10 includes fluid pump 18 downstream of fluid flow sensor 16. Fluid pump 18 is configured to create a negative pressure (i.e., vacuum or suction) on catheter 12, e.g., to draw fluid through an inner lumen of catheter 12 into discharge fluid reservoir 34. For example, fluid pump 18 may include a port configured to couple to aspiration tubing 30, such that the negative pressure created by fluid pump 18 may be applied to the port and through aspiration tubing 30 and other portions of a fluid pathway between aspiration tubing 30 and an inner lumen of catheter 12. As an example of operation of fluid pump 18, when the one or more distal openings 36 of catheter 12 are not blocked, fluid pump 18 may draw fluid from catheter 12 into a discharge fluid reservoir 34 through aspiration tubing 26, 28, 30, and through switch 14 and fluid flow sensor 16. As another example, when the one or more distal openings 36 are partially or wholly blocked, fluid pump 18 may draw fluid from catheter 12 at a reduced flow rate or, in some instances in which blockage is complete, draw no fluid at all. However, even when the one or more distal openings 36 are blocked, fluid pump 18 may be configured to continue to create a vacuum on catheter 12. A variety of pumps may be used for fluid pump 18 including, but not limited to, positive displacement pumps, centrifugal pumps, and the like.

In some examples, fluid pump 18 may be configured for bi-directional operation. For example, fluid pump 18 may be configured to create a negative pressure that draws fluid from catheter 12 in a first flow direction and create a positive pressure that pumps fluid to catheter 12 and through an inner lumen of catheter 12 in a second, opposite flow direction. As an example of this bi-directional operation, an operator of aspiration system 10 may operate pump 18 to pump an aspiration/irrigating fluid, such as saline, from an aspiration fluid reservoir 32 to flush and/or prime catheter 12 (e.g., an infusion state) and subsequently draw fluid from a site of catheter 12, such as saline and/or blood, from catheter 12 (e.g., an aspiration state) into discharge fluid reservoir 34. As another example of bidirectional operation, fluid pump 18 may be configured to simultaneously pump aspiration fluid from aspiration fluid reservoir 32 to catheter 12, such as through an outer catheter (not shown in FIG. 1) within which catheter 12 is positioned or through a lumen of a multi-lumen catheter 12, and draw fluid from catheter 12 (e.g., through an inner lumen of catheter 12 if used with an outer catheter or through a different lumen of a multi-lumen catheter 12) into discharge fluid reservoir 34.

In some examples, aspiration system 10 may include fluid switch 14 to control fluid flow through aspiration system 10. Fluid switch 14 may be configured to start and stop fluid flow from catheter 12 to fluid pump 18 (or in the opposite direction). For example, fluid flow switch 14 may have an "open" position corresponding to flow of fluid through fluid switch 14 and a "closed" position corresponding to no flow of fluid through fluid switch 14. A variety of switching mechanisms may be used for fluid flow switch 14 including, but not limited to, valves, sliders, and the like. In some examples, fluid switch 14 may be configured for unaided operation by a clinician. For example, a mechanism of blocking fluid flow through fluid flow switch 14 may be directly operable by a mechanical force provided by the clinician.

In some examples, fluid switch 14 may be ergonomically positioned such that a clinician operating aspiration system 10 may control flow of fluid using fluid switch 14 and receive feedback from fluid flow sensor 16 using a single hand. For example, a clinician may guide catheter 12 through vasculature of a patient using a first hand, and control and sense fluid flow with a second hand. In this way, aspiration system 10 may enable control of aspiration system 10 by a single clinician and without a clinician diverting her focus while positioning catheter 12. In some examples, fluid flow switch 14 may be less than about ten centimeters from fluid flow sensor 16. For example, fluid switch 14 may be coupled to flow oscillator 20 by aspiration tubing 28 that is less than or equal to ten centimeters. In some examples, a clinician operating aspiration system 10 may hold both fluid switch 14 and fluid flow sensor 16 in one hand at a same time, such that fluid switch 14 is positioned at her thumb for control of a switch of fluid switch 14 and fluid flow sensor 16 is positioned in her palm for haptic feedback from fluid flow sensor 16.

Aspiration system 10 includes fluid flow sensor 16. Fluid flow sensor 16 may be configured to provide haptic feedback of fluid flow from catheter 12. As explained above, a change in fluid flow during an aspiration procedure may indicate to a clinician operating aspiration system 10 whether a condition of the aspiration procedure has been met. For example, absence of, presence of, and/or changes in fluid flow may indicate to a clinician operating aspiration system 10 that a condition related to engagement of catheter 12 with a thrombus has occurred. Fluid flow sensor 16 is configured to provide the clinician with an indication of the presence or absence of fluid flow through an inner lumen of catheter 12, where this indication may be detected by the clinician without the clinician diverting her vision from another aspect of the aspiration procedure, such as an x-ray screen.

Fluid flow sensor 16 includes a fluid inlet 22 configured to receive fluid from catheter 12, either directly or indirectly through other tubing and/or other structures such as switch 14. In some examples, fluid inlet 22 may be configured to attach to aspiration tubing 28, switch 14, or another fluid conduit upstream of fluid flow sensor 16. Fluid flow sensor 16 includes a fluid outlet 24 configured to discharge the fluid received from catheter 12. For example, fluid outlet 24 may be configured to attach to aspiration tubing 30, pump 18, or another fluid conduit downstream of fluid flow sensor 16. Each of fluid inlet 22 and fluid outlet 24 may include other components for attaching to other components of system 10, such as tubing connectors. In some examples, each of fluid inlet 22 and fluid outlet 24 are configured to couple to aspiration tubing, such as aspiration tubing 26, 28, or 30.

Fluid flow sensor 16 may be positioned in aspiration system 10 at a variety of locations. For example, while shown coupled between fluid pump 18 and fluid switch 14, fluid flow sensor 16 may be positioned at any suitable location between fluid pump 18 and a proximal end of catheter 12, such that fluid flow sensor 16 may be in a sterile field. In some examples, fluid flow sensor 16 may be removeable from aspiration system 10. For example, a clinician may want to remove fluid flow sensor 16 from aspiration system 10. In this instance, the clinician may decouple fluid inlet 22 and/or fluid outlet 24 from a respective aspiration tubing 28 and/or aspiration tubing 30 and link aspiration tubing 28 directly to aspiration tubing 30, such as through an adapter (not shown). In this way, fluid flow sensor 16 may be selectively incorporated into aspiration system 10. In some examples, fluid inlet 22 and/or fluid outlet 24 may include structures for restricting flow during decoupling of fluid flow sensor 16, such as coupling adapters that remain coupled to aspiration tubing 28 and/or 30, such that flow oscillator 20 may be removable from fluid inlet 22 and/or fluid outlet 24. In this way, flow oscillator 20 may be removed from aspiration system 10 without causing significant leakage of fluid from aspiration system 10 during decoupling.

Within fluid flow sensor 16, flow oscillator 20 is configured to oscillate flow of the fluid through fluid flow sensor 16 to generate flow-induced vibrations. For example, structural characteristics or components of flow oscillator 20 may be configured to produce two or more states of alternating stability for one or more jets of a fluid within flow oscillator 20. Fluid flow may oscillate between the two or more states to produce sweeping or pulsating motions of the jets through one or more channels or chambers of flow oscillator 20.

These sweeping or pulsating motions may produce vibrations in a housing of the fluid flow sensor that may be felt by holding or contacting the housing. For example, oscillating jets of fluid may impact walls or structures of the housing of the fluid flow sensor at a frequency proportional to a frequency of the oscillations. In this way, kinetic energy from fluid flow may be used to create vibrations capable of detection by an operator of aspiration system 10. A variety of designs may be used for flow oscillator 20 including, but not limited to, feedback-channel fluid oscillators, and the like.

In some examples, flow oscillator 20 may be configured to allow bidirectional flow with unidirectional flow indication. For example, flow oscillator 20 may be configured to oscillate fluid flow in a first flow direction and refrain from oscillating fluid flow in a second flow direction. For example, flow oscillator 20 may be configured to generate vibrations capable of unaided haptic detection by a human for flow in a first direction and generate vibrations that are not capable of unaided haptic detection by a human for flow in a second direction. In some examples, flow oscillator 20 is configured to oscillate the flow of the fluid above a haptic threshold in a first flow direction and not oscillate the flow of the fluid above the haptic threshold in a second flow direction. For example, vibrations produced by flow oscillator 20 capable of unaided detection by a clinician may correspond to a "haptic threshold," above in which the vibrations may be detected by the clinician and below which the vibrations may not be detected by the clinician. While this haptic threshold may vary depending on a sensitivity of the clinician, the difference between the vibrations produced by flow of fluid in the first flow direction and the vibrations produced by flow of fluid in the second flow direction may be of such a degree (e.g., an order of magnitude or periodicity) that the clinician would note a difference between fluid flowing in the first flow direction and the second flow direction.

Flow oscillator 20 further comprises at least one channel or chamber configured to pass fluid from fluid inlet 22 to fluid outlet 24. In some examples, a cross-sectional area of the at least one channel may be greater than a cross-sectional area of aspiration tubing 28. For example, flow oscillator 20 may create a pressure drop for fluid entering the at least one channel. Additionally or alternatively, in some examples, an inner diameter of the at least one channel may be greater than an inner diameter of the lumen of catheter 12 from which fluid flow sensor 16 receives fluid.

Flow oscillator 20 may be manufactured from any suitable material including, but not limited to, polymers, metals, and the like. In some examples, flow oscillator 20 is manufactured using injection molding or three-dimensional (3D) printing. For example, as will be discussed further below, flow oscillator 20 may be configured to oscillate fluid flow through fluid flow sensor 16 without moving parts. As such, inexpensive manufacturing techniques such as injection molding and 3D printing may be used to manufacture flow oscillator 20.

In some examples, fluid flow sensor 16 includes a pressure sensor configured to detect flow of the fluid. For example, while fluid flow sensor 16 may be configured to produce flow-induced vibrations, amplification, recording, or some other post-processing of the vibrations may be desired. As such, the pressure sensor may be kinetically coupled to (i.e., coupled to receive kinetic energy from) flow oscillator 20 of fluid flow sensor 16, such that vibrations from flow oscillator 20 may be detected by the pressure sensor. In some examples, the pressure sensor is communicatively coupled to a notification system configured to generate a notification in response to detecting the flow of the fluid. For example, a pressure signal from the pressure sensor may be sent to sensing or notification circuitry. In response to receiving the pressure signal, the sensing or notification circuitry may create a visual or audible notification representing a flow characteristic of the fluid flow, such as a presence of, absence of, change in, or degree of fluid flow. The sensing or notification circuitry may include alarms, visual indicators (e.g., light emitting diodes (LEDs)), or the like. A variety of pressure sensors may be used including, but not limited to, pressure transducers, accelerometers, and the like.

Fluid flow sensor 16 may be selected for a variety of flow conditions including, but not limited to, flow rate, pressure drop across fluid flow sensor 16, and the like. In some examples, fluid flow sensor 16 may be configured to produce vibrations at a flow rate between about 1 milliliter per second and about 10 milliliters per second. Fluid flow sensor 16 may be selected to produce vibrations having a variety of characteristics. Example characteristics may include, but are not limited to, amplitude of vibrations, frequency of vibrations, and the like. In some examples, flow oscillator 20 is configured to generate vibrations having a frequency between about 15 hertz and about 30 hertz at a flow rate of the fluid between about 3 milliliters per second and about 5 milliliters per second.

In some examples, flow oscillator 20 may be configured to increase a magnitude of the vibrations in response to an increase in a flow rate of the fluid through flow oscillator 20. For example, flow oscillator 20 may include a moveable oscillating portion configured to impact one or more structures within flow oscillator 20 with a greater amount of force as a flow rate of fluid through flow oscillator 20 increases. In some examples, flow oscillator 20 may be configured to increase a frequency of the vibrations in response to an increase in a flow rate of the fluid through flow oscillator 20. For example, flow oscillator 20 may include a flow diverting portion configured to oscillate flow between two or more states at a rate that is proportional to a flow rate of fluid through flow oscillator 20. In this way, a clinician operating aspiration system 10 may receive an indication of both a presence of fluid flow, indicated by a presence of vibrations, and a change in a degree of fluid flow, indicated by either a change in magnitude of the vibrations or a change in frequency of the vibrations.

In some examples, flow oscillator 20 may be configured to change at least one of an amplitude of the vibrations or a frequency of the vibrations in response to a change in density of the fluid flowing through flow oscillator 20. For example, saline has a density of about 2.16 g/cm3, while blood has a density of about 1.08 $g/cm^3$. As a composition of the fluid removed from catheter 12 changes, such as when a thrombus is engaged by catheter 12, a density of the fluid may change, which may affect flow rate, turbulence, or other flow characteristics that may affect an amplitude or frequency of the vibrations. For example, a change in amplitude and/or frequency of the vibrations may occur when the composition of the fluid removed from catheter 12 changes from undiluted blood (or substantially undiluted blood) to a mixture of saline and blood, to undiluted saline (or substantially undiluted saline), or from one to another of any of the foregoing. This change in the vibrations can provide useful information to the operator, including confirmation that the aspiration of vessel contents (blood and/or thrombus) has commenced, and that any saline left in the catheter 12 (e.g. from priming or flushing) has been removed. This may in turn function as a notice to the operator that the some or all of the thrombus may now be in the canister, and further that some adjustment to the aspiration procedure (e.g. a distal advancement, or a full withdrawal) is now appropriate.

In some examples, all or just parts of flow oscillator 20 through which fluid flow may be coated with at least one of an anti-thrombogenic material or a lubricious material. For example, fluid received from catheter 12 may include tissues, such as pieces of a thrombus, suspended in the fluid. These tissues may bind to walls of channels or chambers within flow oscillator 20, such that flow through flow oscillator 20 may be changed. By including an anti-thrombogenic material or a lubricious material in flow oscillator 20, tissues suspended in the fluid may be less likely to bind to flow oscillator 20.

In some examples, flow oscillator 20 may be free of moving parts. For example, flow fluid oscillator 20 may comprise a plurality of channels and/or chambers configured to oscillate flow of fluid through flow oscillator 20. The plurality of channels may be more resistant to clogging or breaking than flow sensors that include moving parts. As such, fluid flow sensor 16 may reliably operate with fewer parts that may malfunction, stick, or change in operation. In some examples, fluid flow sensor 16 may be free of electronics. For example, a housing of flow oscillator 20 may receive kinetic energy from oscillating jets of fluid flow, thereby generating vibrations. As such, fluid flow sensor 16 may operate without an external power source, such as a power supply or battery.

Figure 2A:
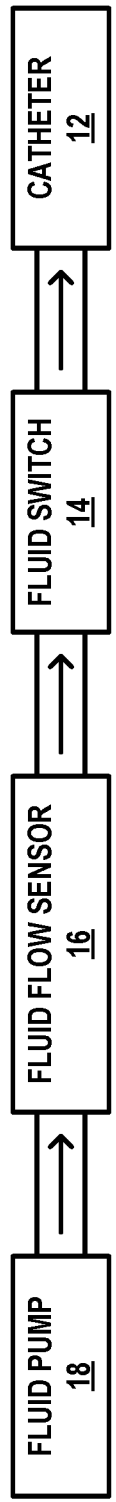
FIG. 2A is conceptual block diagram illustrating the aspiration system of FIG. 1 at an infusion state.

FIG. 2A is conceptual block diagram illustrating aspiration system 10 of FIG. 1 at an infusion state. For example, aspiration system 10 may operate in an infusion state when flushing components of aspiration system 10 and/or delivering fluid (e.g., a therapeutic agent or a fluid configured to aid aspiration) to a treatment site in vasculature of a patient. In the infusion state, fluid pump 18 pumps a fluid through fluid flow sensor 16 and fluid switch 14 to catheter 12 in the second flow direction. For example, a clinician may operate fluid pump 18 to generate a positive pressure and may operate fluid switch 14 to be in an "open" position. In some examples, fluid flow sensor 16 may be configured pass the aspiration fluid through fluid flow sensor 16 without generating vibrations capable of detection by the clinician operating aspiration system 10.

Figure 2B:
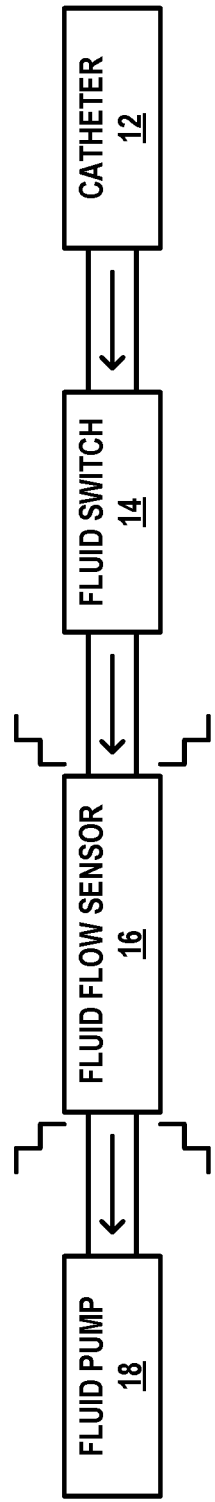
FIG. 2B is a conceptual block diagram illustrating the aspiration system of FIG. 1 at an unblocked aspiration state.

FIG. 2B is a conceptual block diagram illustrating aspiration system 10 of FIG. 1 at an unblocked aspiration state. For example, aspiration system 10 may operate in an unblocked aspiration state when drawing fluid from a treatment site within vasculature of a patient during positioning of catheter 12 and/or in an attempt to withdraw a thrombus after catheter 12 has been positioned. In the unblocked aspiration state, fluid pump 18 draws fluid from catheter 12 through fluid switch 14 and fluid flow sensor 16 to fluid pump 18. For example, a clinician may operate fluid pump 18 to generate a negative pressure and may operate fluid switch 14 to be in an "open" position. Fluid flow sensor 16 may be configured pass the aspiration fluid through fluid flow sensor 16 while generating vibrations capable of detection by the clinician operating aspiration system 10. For example, fluid flow sensor 16 may oscillate the flow of the fluid from catheter 12 and through fluid flow sensor 16 to generate the vibrations.

Figure 2C:
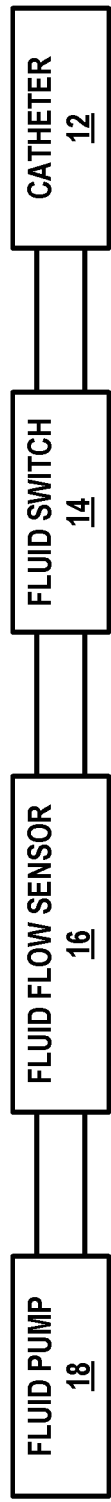
FIG. 2C is a conceptual block diagram illustrating the aspiration system of FIG. 1 at a blocked aspiration state.

FIG. 2C is a conceptual block diagram illustrating aspiration system 10 of FIG. 1 at a blocked aspiration state. For example, aspiration system 10 may operate in a blocked aspiration state after catheter 12 has engaged the thrombus such that the thrombus is partially or fully blocking distal opening 36 of catheter 12. In the blocked aspiration state, fluid pump 18 may draw reduced amounts of fluid from catheter 12 through fluid switch 14 and fluid flow sensor 16 to fluid pump 18. For example, a clinician may operate fluid pump 18 to generate a negative pressure and may operate fluid switch 14 to be in an "open" position. Fluid flow sensor 16 may be configured pass any aspiration fluid through fluid flow sensor 16 at a reduced rate, including no passage of fluid. In this circumstance, fluid flow sensor 16 oscillates or vibrates at a reduced frequency or magnitude, or not at all.

Figure 3A:
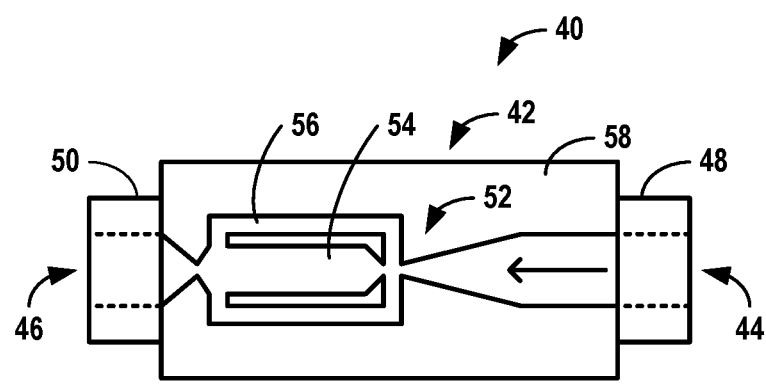
FIG. 3A is a diagram of a fluid flow sensor that includes a flow oscillator having a flow diverting portion.

As explained above, fluid flow sensors discussed herein may be configured to oscillate flow of fluid, such as a fluid jet or stream, at least within the fluid flow sensors. In some examples, fluid flow sensors discussed herein may generate flow-induced vibrations by diverting fluid within a flow oscillator. FIG. 3A is a diagram of an example fluid flow sensor 40 that includes a flow oscillator 42 including a flow diverting portion 52. Fluid flow sensor 40 is an example of fluid flow sensor 16 of FIG. 1. Fluid flow sensor 40 may include a fluid inlet 44 configured to receive fluid from catheter 12 either directly or indirectly through aspiration tubing and/or other structures such as switch 14. Fluid inlet 44 includes an inlet connector 48 that may be configured to couple to a fluid conduit such as aspiration tubing or a fluid switch. Fluid flow sensor 40 includes a fluid outlet 46 configured to discharge the fluid. Fluid outlet 46 includes an outlet connector 50 that may be configured to couple to a fluid conduit, such as aspiration tubing 30 or a fluid pump 18.

Fluid flow sensor 40 includes flow oscillator 42 configured to oscillate flow of the fluid through fluid flow sensor 40 to generate flow-induced vibrations. In the example of FIG. 3A, flow oscillator 42 includes a housing 58 and a flow diverting portion 52 configured to oscillate the flow of the fluid to generate an oscillating pressure differential. Flow diverting portion 52 includes a primary channel 54 configured to pass a majority of the flow of the fluid as a primary jet. Primary channel 54 may receive the primary jet of fluid from fluid inlet 44 and discharge at least a portion of the primary jet through fluid outlet 46. As shown, in some examples, primary channel 54 may be directly in line with flow from fluid inlet 44, which may enable primary channel 54 to be relatively resistant to clogging by tissue in the fluid.

Flow diverting portion 52 also includes at least two secondary (e.g., feedback) channels 56 each configured to divert a portion of the flow of the fluid from a downstream portion of the primary jet from primary channel 54 to an upstream portion of the primary channel 54 as a secondary jet. These diverted secondary jets may intersect the primary jet, causing the primary jet to change a shape based on a pressure differential between the two secondary jets. The changed shape may cause a change in the pressure differential, such that the pressure differential oscillates between the secondary jets. In this way, the primary jet may oscillate within primary channel 54. These oscillations may generate vibrations, which may be felt on housing 58.

Figure 3B:
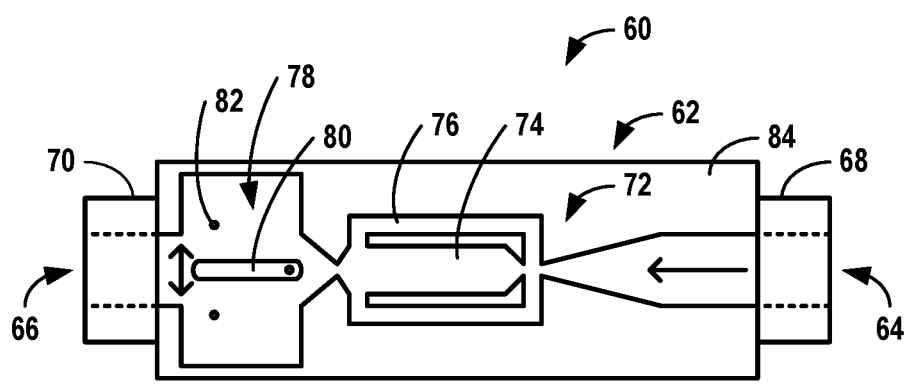
FIG. 3B is a diagram of a fluid flow sensor that includes a flow oscillator having a flow diverting portion and an oscillating portion.

In some examples, fluid flow sensors discussed herein may generate flow-induced vibrations by diverting fluid within a flow oscillator and oscillating a mechanical structure using the diverted fluid. FIG. 3B is a diagram of an example fluid flow sensor 60 that includes a flow oscillator having a flow diverting portion 72 and an oscillating portion 78. Fluid flow sensor 60 is an example of fluid flow sensor 16 of FIG. 1. Fluid flow sensor 60 may include a fluid inlet 64 configured to receive fluid from catheter 12. Fluid inlet 64 includes an inlet connector 68 that may be configured to couple to a fluid conduit such as aspiration tubing or a fluid switch. Fluid flow sensor 60 includes a fluid outlet 66 configured to discharge the fluid. Fluid outlet 66 includes an outlet connector 70 that may be configured to couple to a fluid conduit, such as aspiration tubing or a fluid pump.

Fluid flow sensor 60 includes flow oscillator 62 configured to oscillate flow of the fluid through fluid flow sensor 60 to generate flow-induced vibrations. In the example of FIG. 3B, flow oscillator 62 includes a housing 84 and a flow diverting portion 72 configured to oscillate the flow of the fluid to generate an oscillating pressure differential. Flow diverting portion 72 includes a primary channel 74 and at least two secondary channels 76, which may be operably similar to flow diverting portion 52 described in FIG. 3A. An oscillating jet of fluid may be discharged from flow diverting portion 72.

Flow oscillator 62 also includes an oscillating portion 78 configured to oscillate in response to the oscillating pressure differential. As explained above, flow diverting portion 72 creates an oscillating pressure differential that produces an oscillating jet of fluid. Oscillating portion 78 may include an oscillation structure 80 and at least one amplification structure 82. Oscillating structure 80 may be configured to oscillate in response to oscillation of the oscillating jet. For example, oscillating structure 80 may include a pivot or flexible structure that allows oscillating structure 80 to oscillate in response to oscillations of the oscillating jet. Amplification structure 82 may be configured to contact oscillating structure 80 to increase an amplitude of vibration caused by the oscillating jet. For example, as a flow rate of the oscillating jet increases, a magnitude of impact of oscillating structure 80 on amplification structure 82 may increase, such that an amplitude of vibration may increase. In some examples, oscillating structure 80 comprises at least one of a flap, a roller, a ball, or a paddle, or combinations thereof. In this way, vibrations caused by oscillating flow of flow oscillator 62 may be modified. These oscillations may generate vibrations, such as may be felt on housing 84.

Figure 4:
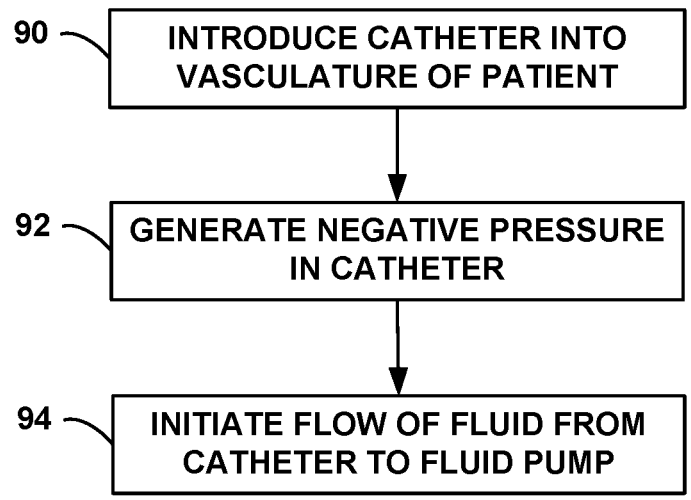
FIG. 4 is a flow diagram of an example method of aspiration that includes generating flow-induced vibrations using a fluid flow sensor in response to receiving fluid flow from a catheter.

FIG. 4 is a flow diagram of an example method of aspiration that includes generating flow-induced vibrations using a fluid flow sensor in response to receiving fluid flow from a catheter. The techniques of FIG. 4 are described with reference to the various aspects of aspiration system 10 of FIG. 1 for illustrative purposes, however, such descriptions are not intended to be limiting and the techniques of FIG. 4 may be used to form other aspiration systems. The technique of FIG. 4 include introducing catheter 12 into vasculature of the patient (90) and aspirating a thrombus by generating negative pressure on catheter 12 (92), and initiating flow of fluid from catheter 12 to fluid pump 18 (94), thereby generating vibrations in response to flow of fluid through fluid flow sensor 16. In some examples, the techniques described herein include removing catheter 10 from the vasculature of the patient once the procedure is complete.

In some examples, introducing catheter 10 into vasculature of a patient (90) may be aided by initially introducing a guidewire, guide catheter or another guide member into the vasculature of the patient to a target treatment site. An elongated body of catheter 12 may then be introduced over the guidewire and advanced to the target treatment site. Additionally, or alternatively, catheter 12 may be introduced into vasculature of a patient via the aid of a guide catheter. For example, that the guide catheter may be initially introduced into vasculature of a patient and positioned adjacent a target treatment site. Catheter 12 may then be introduced through an inner lumen of the guide catheter. In some examples, catheter 12 is inserted into vasculature of the patient prior to attachment of a remainder of aspiration system 10, while in other examples, catheter 18 may be inserted into vasculature of the patient with a remainder of aspiration system 10 already attached, such as through aspiration tubing 26.

The technique of FIG. 4 also includes various steps for initiating aspiration to remove a thrombus. For example, a distal end of catheter 12 may be introduced into an intracranial blood vessel and positioned adjacent to and/or proximal of a thrombus. Once catheter 12 is in place, a clinician may flush aspiration system 10 with an aspiration fluid, such as saline. For example, a clinician may control fluid pump 18 to generate a positive pressure to discharge fluid from a port of fluid pump 18.

The technique of FIG. 4 includes generating a negative pressure in catheter 12 (92). For example, once the at least one opening 36 of catheter 12 is positioned at a position corresponding to an estimated location of the thrombus, a clinician operating aspiration system 10 may operate fluid pump 18 to generate the negative pressure on a port coupled to aspiration tubing 30. This negative pressure may be configured to produce a desired flow rate, pressure drop, or other flow condition responsive to a change in pressure.

The technique of FIG. 4 includes initiating flow of fluid from catheter 12 to fluid pump 18 (94). In examples in which aspiration system 10 does not include a flow switch, initiating of flow of fluid may correspond to generating the negative pressure, such that fluid pump 18 may operate to control the negative pressure to control flow of the fluid. In examples in which aspiration system 10 includes flow switch 14, once the negative pressure has been generated, the clinician operating aspiration system 10 may operate flow switch 14 to an "open" position to initiate flow of fluid from catheter 12 through flow switch 14 and fluid flow sensor 16 to fluid pump 18.

The clinician may sense, either directly or indirectly, vibrations generated in response to flow of fluid through fluid flow sensor 16. As fluid flows from catheter 12 to fluid pump 18, fluid flow sensor 16 may oscillate flow of the fluid through fluid flow sensor 16 to generate flow-induced vibrations. In some examples, such as examples in which fluid flow sensor 16 is configured to vibrate above an oscillation threshold at flow rates above a particular fluid flow and not vibrate or vibrate below the oscillation threshold at flow rates below the particular fluid flow, the presence or absence of vibrations may indicate to the clinician holding fluid flow sensor 16 that fluid is or is not, respectively, flowing from catheter 12 to fluid pump 18. In examples in which a flow rate of fluid flow corresponds to a magnitude or frequency of vibrations, a change in magnitude or frequency of vibrations may indicate to the clinician holding fluid flow sensor 16 that a fluid flow rate is changing.

Catheter 12 may be removed from the vasculature once the procedure is complete.

Figure 5:
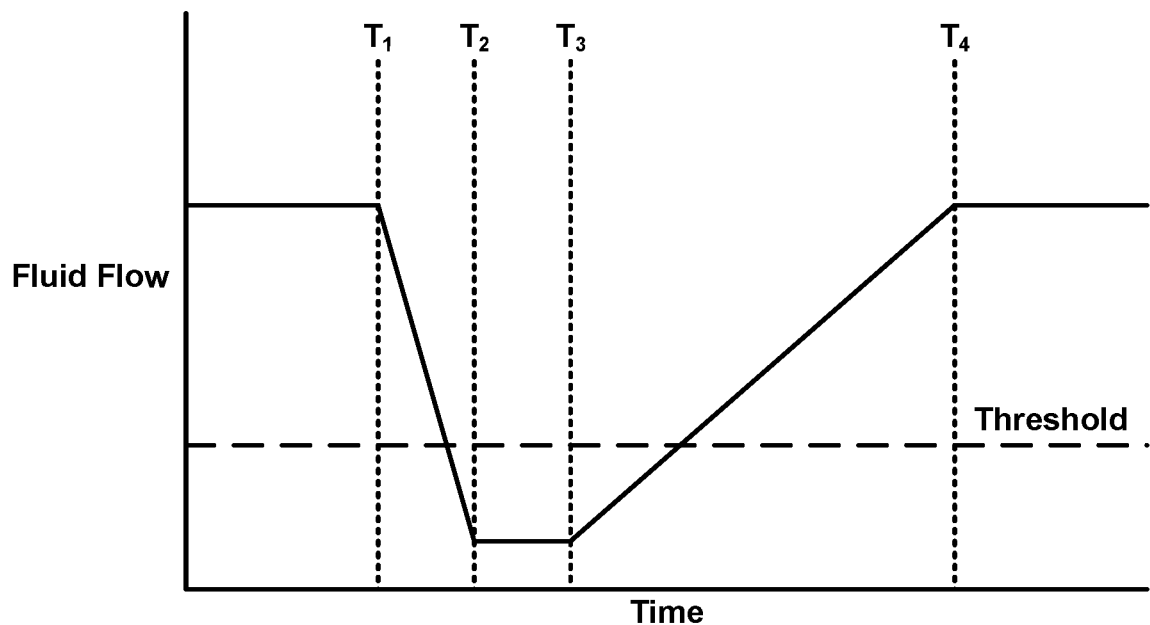
FIG. 5 is an illustrative example graph of fluid flow versus time for an example aspiration procedure using an aspiration system.

As the thrombus is suctioned from the blood vessel through an inner lumen of catheter 12, fluid flow sensor 16 may provide the clinician operating aspiration system 10 with a haptic indication of fluid flow that indicates a condition related to engagement of the thrombus. FIG. 5 is an illustrative example graph of fluid flow versus time for an example aspiration procedure using aspiration system 10, such fluid flow being used to generate vibrations in fluid flow sensor 16.

In the example of FIG. 5, the clinician may position the at least one opening 36 of catheter 12 near the thrombus, such that the thrombus partially blocks the at least one opening 36 ($T_1$). As a result of this partial blockage, the flow of fluid from catheter 12 to fluid pump 18, and thereby through fluid flow sensor 16, may be reduced. In examples in which a frequency or magnitude of vibrations generated by fluid flow sensor 16 corresponds to a flow rate of fluid through fluid flow sensor 16, this reduction in flow rate may cause a corresponding change in magnitude or frequency of vibrations, thereby providing an indication to the clinician that the thrombus has been at least partially engaged.

In the example of FIG. 5, as the thrombus becomes further engaged, the thrombus may fully or substantially fully block the at least one opening 36 of catheter 12 (T2). For example, a flow of fluid may continue to decrease as a thrombus is drawn into catheter 12 and begins to more fully block the at least one opening 36 of catheter 12. In examples in which fluid flow sensor 16 is configured to produce vibrations above a particular fluid flow threshold ("Threshold"), at a certain reduction in fluid flow, fluid flow sensor 16 may produce vibrations that are below a haptic level of the clinician, or may produce no vibrations at all. This lack of haptic feedback may indicate to the clinician that flow of fluid has stopped or substantially stopped, thus indicated that the thrombus is fully engaged by catheter 12. In some examples, not shown in FIG. 5, the thrombus may be removed by removing catheter 12 while the thrombus is fully engaged with catheter 12.

In the example of FIG. 5, as pieces of the thrombus are removed, such as by circulating a small amount of aspiration fluid (e.g., saline) through catheter 12 or oscillating positive and negative pressure to catheter 12 from fluid pump 18, pieces of thrombus may be removed, such that fluid flow may begin to increase (T3). As fluid flow increases, the fluid flow may exceed the particular fluid flow threshold such that fluid flow sensor 16 may begin producing vibrations that may be detected by the clinician and that correspond to fluid flow through from catheter 12 to fluid pump 18. These vibrations may indicate to the clinician that fluid is flowing from catheter 12 to fluid pump 18, such that removal of the thrombus is progressing. In some instances, such presence of vibrations may indicate to the clinician that the clinician may reposition catheter 12, such as by advancing catheter 12 further into vasculature of the patient. If the fluid flow decreases or drops below the fluid flow threshold such that vibrations from fluid flow sensor 16 are reduced or absent, this change in vibrations may indicate to the clinician the more of the thrombus may be removed. If the fluid flow does not decrease or drop below the fluid flow threshold such that vibrations form fluid flow sensor 16 are not reduced and remain present, this lack of reduction in vibrations may indicate to the clinician that the thrombus has been removed. In the example of FIG. 5, the fluid flow may return to an unblocked fluid flow rate once the thrombus is removed ($T_4$).

Various aspects of the disclosure have been described. These and other aspects are within the scope of the following claims.

What is claimed is:

1. An aspiration system, comprising:
    a catheter; and
    a fluid flow sensor comprising:
        a fluid inlet configured to receive fluid from the catheter;
        a fluid outlet configured to discharge the fluid; and
        a flow oscillator configured to oscillate flow of the fluid through the fluid flow sensor to generate flow-induced vibrations of a housing of the fluid flow sensor,
    wherein the flow oscillator further comprises:
        a flow diverting portion configured to oscillate the flow of the fluid between the fluid inlet and the fluid outlet to generate an oscillating pressure differential; and
        an oscillating portion downstream of the flow diverting portion,
    wherein the oscillating portion comprises:
        an oscillating structure configured to oscillate in response to the oscillating pressure differential; and
        at least one amplification structure configured to contact the oscillating structure to increase an amplitude of the flow-induced vibrations.

2. The aspiration system of claim 1, wherein the oscillating portion comprises at least one of a flap, a roller, a ball, or a paddle.

3. The aspiration system of claim 1, wherein the flow oscillator is configured to generate vibrations capable of haptic detection by a human for flow in a first direction and generate vibrations that are not capable of haptic detection by a human for flow in a second direction.

4. The aspiration system of claim 1, wherein the flow oscillator is configured to oscillate the flow of the fluid above an oscillation threshold in a first flow direction and not oscillate the flow of the fluid above the oscillation threshold in a second flow direction.

5. The aspiration system of claim 1, wherein each of the fluid inlet and the fluid outlet are configured to couple to aspiration tubing.

6. The aspiration system of claim 5, wherein the flow oscillator further comprises at least one channel, and wherein a cross-sectional area of the at least one channel is greater than a cross-sectional area of an inner lumen of the aspiration tubing.

7. The aspiration system of claim 1, wherein the flow oscillator further comprises at least one channel, and wherein an inner diameter of the at least one channel is greater than an inner diameter of the catheter.

8. The aspiration system of claim 1, wherein the flow oscillator further comprises:
    at least one primary channel configured to pass a majority of the flow of the fluid; and
    at least two secondary channels each configured to divert a portion of the flow of the fluid from a downstream portion of the at least one primary channel to an upstream portion of the at least one primary channel.

9. The aspiration system of claim 1, further comprising a pressure sensor mechanically coupled to the fluid flow sensor and configured to detect the flow-induced vibrations from the housing of the fluid flow sensor indicating flow of the fluid through the fluid flow sensor.

10. The aspiration system of claim 9, wherein the pressure sensor is configured to communicatively couple to a notification system configured to generate a notification in response to detecting the flow of the fluid.

11. The aspiration system of claim 1, wherein the flow oscillator is configured to generate vibrations having a frequency of about 15 hertz to about 30 hertz at a flow rate of the fluid of about 3 milliliters per second to about 5 milliliters per second.

12. The aspiration system of claim 1, wherein the flow oscillator is configured to increase a magnitude of the flow-induced vibrations in response to an increase in a flow rate of the fluid through the flow oscillator.

13. The aspiration system of claim 1, wherein the flow oscillator is configured to increase a frequency of the flow-induced vibrations in response to an increase in a flow rate of the fluid through the flow oscillator.

14. The aspiration system of claim 1, further comprising a fluid switch configured to start and stop the flow of the fluid through the flow oscillator.

15. The aspiration system of claim 14, wherein the fluid switch is coupled to the flow oscillator by ten or less centimeters of aspiration tubing.

16. The aspiration system of claim 1, wherein the catheter is upstream of the fluid flow sensor, the aspiration system further comprising a fluid pump downstream of the fluid flow sensor and configured to generate a suction through the catheter.

17. The aspiration system of claim 1, wherein the flow oscillator is coated with at least one of an anti-thrombogenic material or a lubricious material.

* * * * *